(12) United States Patent
Helland et al.

(10) Patent No.: US 7,353,067 B1
(45) Date of Patent: Apr. 1, 2008

(54) IMPLANTABLE LEADS, ELECTRODE PORTIONS AND METHODS FOR SECURING

(75) Inventors: John R. Helland, Saugus, CA (US); Gene A. Bornzin, Simi Valley, CA (US)

(73) Assignee: Pacesetter, Inc., Sylman, CA (US)

( * ) Notice: Subject to any disclaimer, the term of this patent is extended or adjusted under 35 U.S.C. 154(b) by 491 days.

(21) Appl. No.: 10/759,902

(22) Filed: Jan. 16, 2004

(51) Int. Cl.
*A61N 1/05* (2006.01)

(52) U.S. Cl. ..................................... 607/130

(58) Field of Classification Search ............... 607/119, 607/120, 122, 118, 126, 130, 116, 25
See application file for complete search history.

(56) References Cited

U.S. PATENT DOCUMENTS

| | | | |
|---|---|---|---|
| 4,360,031 A * | 11/1982 | White | 607/120 |
| 4,712,555 A | 12/1987 | Thornander et al. | 128/419 PG |
| 4,788,980 A | 12/1988 | Mann et al. | 128/41 PG |
| 4,940,052 A | 7/1990 | Mann et al. | 128/419 PG |
| 4,944,298 A | 7/1990 | Sholder | 128/419 PG |
| 5,203,326 A | 4/1993 | Collins | 128/419 PG |
| 5,466,254 A | 11/1995 | Helland | 607/123 |
| 5,476,483 A | 12/1995 | Bornzin et al. | 607/17 |
| 5,575,814 A * | 11/1996 | Giele et al. | 607/127 |
| 6,004,269 A * | 12/1999 | Crowley et al. | 600/439 |
| 6,006,134 A | 12/1999 | Hill et al. | 607/9 |
| 6,718,212 B2 * | 4/2004 | Parry et al. | 607/130 |
| 7,099,718 B1 * | 8/2006 | Thacker et al. | 607/117 |
| 2003/0074041 A1 | 4/2003 | Parry et al. | 607/130 |

* cited by examiner

*Primary Examiner*—George R. Evanisko
*Assistant Examiner*—Rex Holmes

(57) ABSTRACT

An exemplary lead and sheath assembly suitable for positioning in the human body includes a lead body, a sheath surrounding the lead body, one or more conductors embedded in the lead body and one or more conduits that allow for a flow of adhesive or an adhesive component to a site in the human body to thereby secure one or more electrodes in electrical contact at least one of the conductors. Various methods, devices, systems and/or other assemblies are also disclosed.

20 Claims, 10 Drawing Sheets

EXEMPLARY LEAD CROSS-SECTION
300

EXEMPLARY LEAD AND SHEATH
CROSS-SECTION
400

US 7,353,067 B1

IMPLANTABLE LEADS, ELECTRODE PORTIONS AND METHODS FOR SECURING

TECHNICAL FIELD

Subject matter disclosed herein generally relates to devices, systems and/or methods for providing cardiac pacing therapy. More particularly, various exemplary leads, electrode portions and methods for securing are disclosed.

SUMMARY

An exemplary lead and sheath assembly suitable for positioning in the human body includes a lead body, a sheath surrounding the lead body, one or more conductors embedded in the lead body and one or more conduits that allow for a flow of adhesive or an adhesive component to a site in the human body to thereby secure one or more electrodes in electrical contact with at least one of the conductors. Various methods, devices, systems and/or other assemblies are also disclosed.

The various apparatus and methods described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Exemplary Stimulation Device

The techniques described below are intended to be implemented in connection with any stimulation device that is configured or configurable to stimulate or shock nerves and/or tissue, including, but not limited to, a patient's heart.

Figure 1:
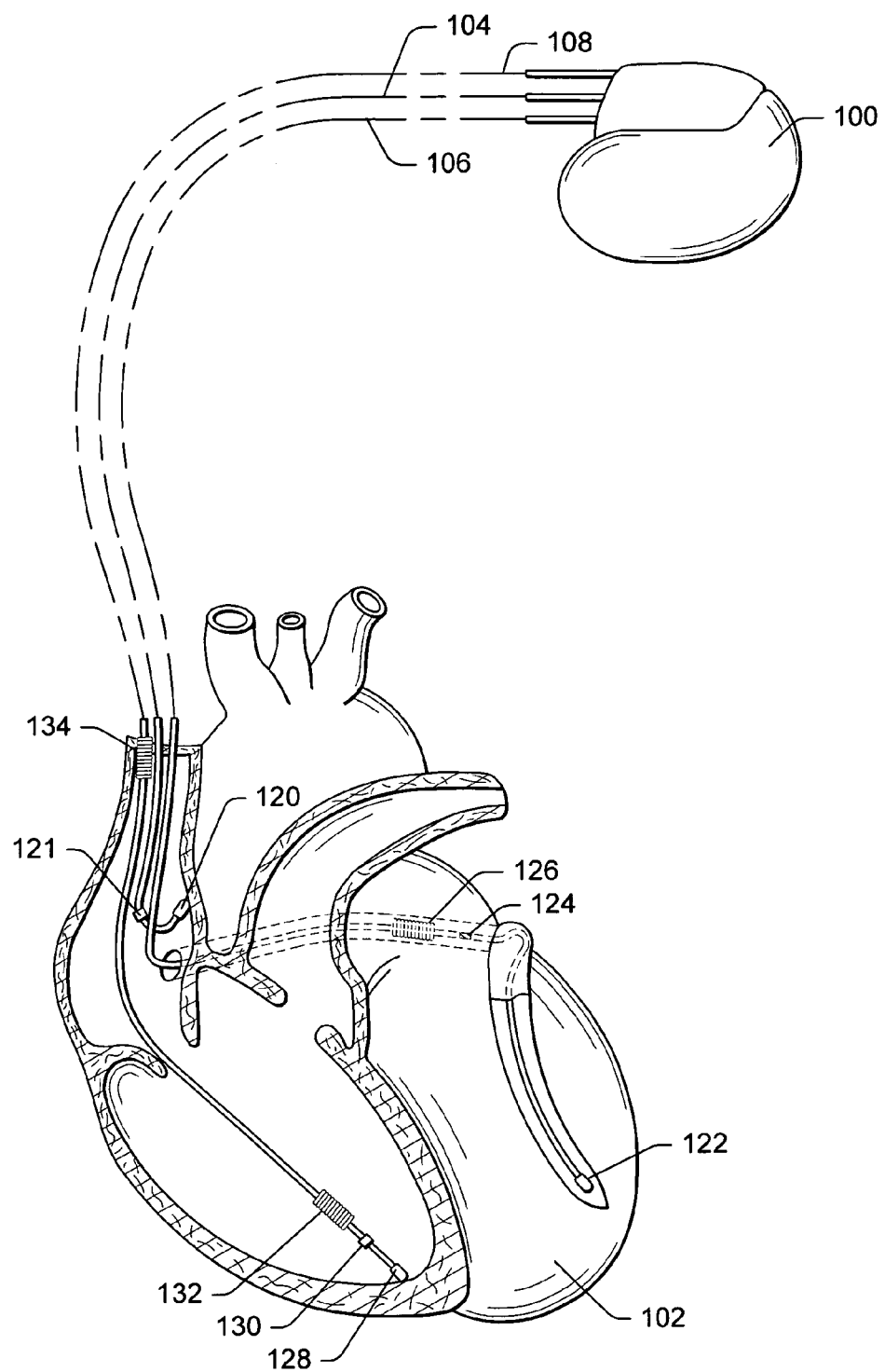
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
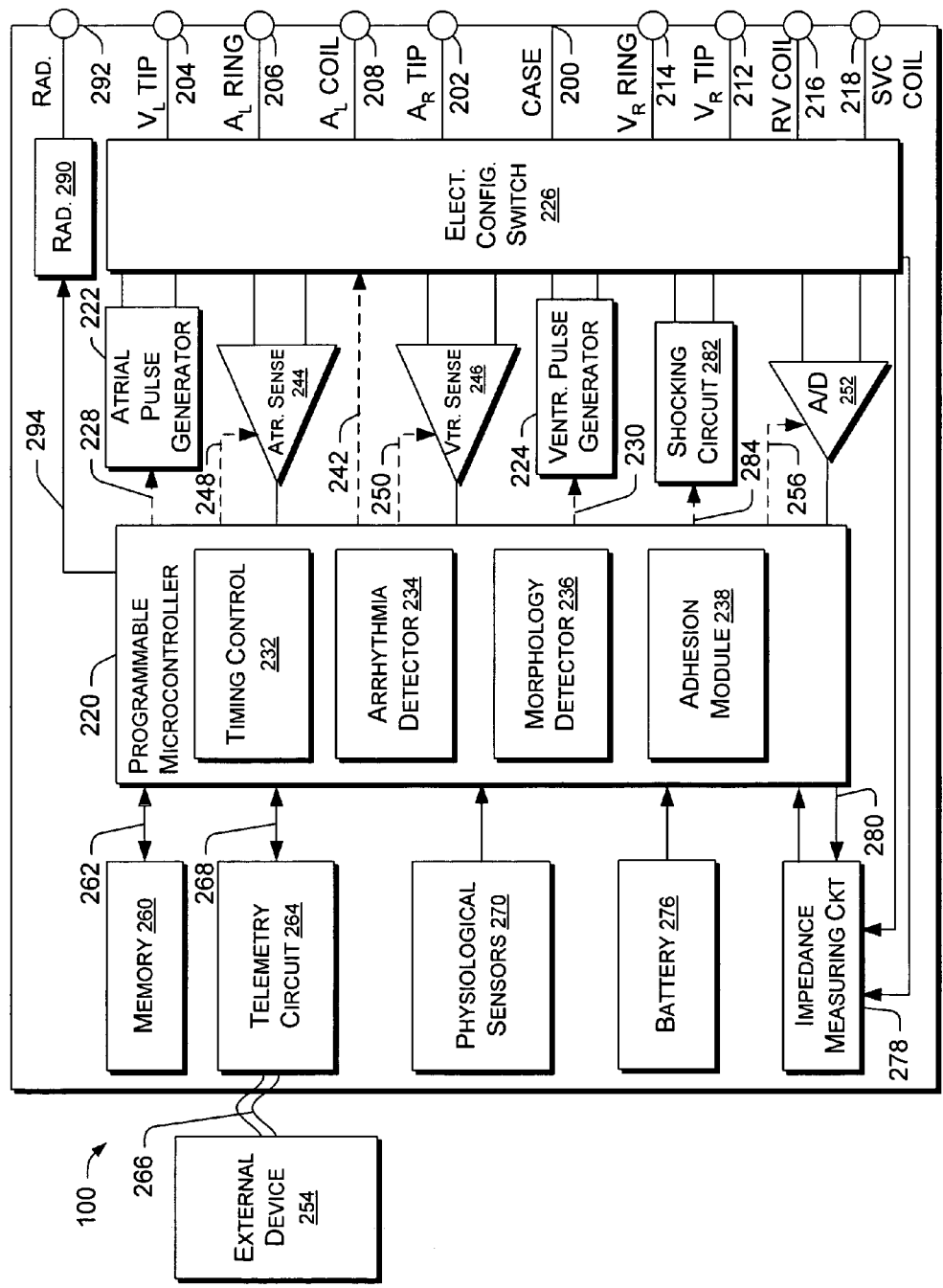
FIG. 2 is a functional block diagram of a multi-chamber implantable stimulation device illustrating basic elements that are configured to provide cardioversion, defibrillation, and pacing stimulation to the heart and/or other tissues stimulation in various places in a patient's body.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. A right atrial ring terminal ($A_R$ RING) may also be included adapted for connection to the atrial ring electrode 121. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 optionally includes an adhesion module 238 for performing a variety of tasks related to use of an exemplary electrode portion, as described in more detail below. This component can be utilized by the stimulation device 100 for aiding in implantation or positioning, adhesion or fixation, removal or de-fixation, electrode selection (configuration, polarity, etc.), and/or administration of various therapies, including tissue stimulation to effect the myocardium and/or other tissue and/or nerves. The adhesion module 238 may be implemented in hardware as part of the microcontroller 220, or as software/firmware instructions programmed into the device and executed on the microcontroller 220 during certain modes of operation. Of course, such an exemplary electrode portion and/or module 238 may be optionally used for sensing. In general, such a module typically includes software and/or hardware for selectively delivering power to one or more electrodes of an electrode portion.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors to help detect movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses. The exemplary device 100 optionally includes an adhesive module 238, a radiation module 290, and/or a radiation connector 292. As described in more detail below, the modules 238, 290 and the connect 292 may perform functions performed by modules or connectors of various exemplary securing units. For example, the adhesive module 238 may direct the radiation module 290 to deliver radiation to a radiation conduit connected to the device 100 via the radiation connector 292. In general, the radiation conduit directs radiation to a site wherein the radiation interacts with material and/or tissue at the site. Various exemplary leads and/or lead and sheath assemblies are described below which optionally include a radiation conduit capable of such operation. Further, various exemplary leads and/or lead and sheath assemblies optionally include one or more conduits and/or channels for delivery of medicaments or other substances, for example, to delay an immune response, to promote tissue growth, inhibit an inflammatory response, activate an immune response, etc.

Figure 3:
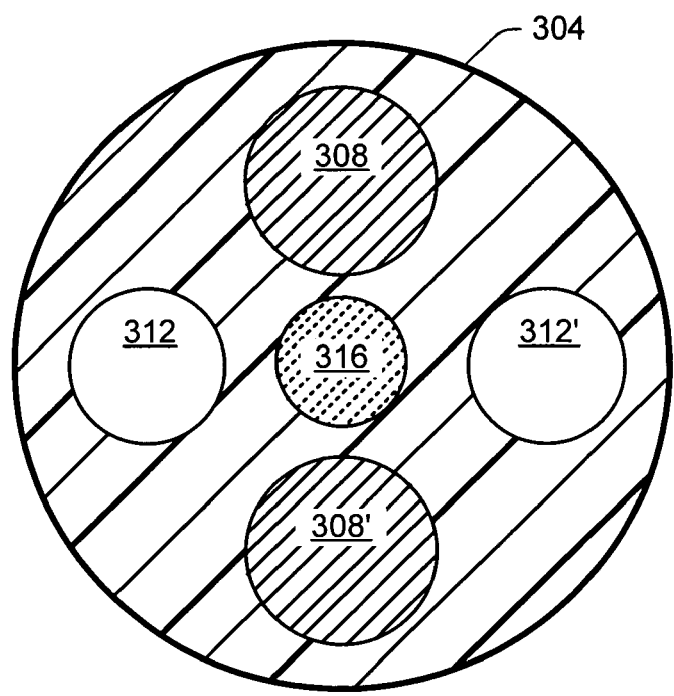
FIG. 3 is a cross-sectional view of an exemplary lead.

FIG. 3 shows a cross-sectional view of an exemplary lead 300. The lead 300 has a proximal end and a distal end and, as shown in the cross-sectional view, includes one or more conductors 308, 308', one or more channels 312, 312', and optionally a radiation conduit 316. A lead body 304 houses the two conductors 308, 308', the two channels 312, 312' and the radiation conduit 316. In general, a lead body is constructed from a flexible insulator that allows for navigation in a patient body or other animal body.

The conductors 308, 308' allow for connection to a stimulation device or securing device at or near the proximal end of the lead 300 and to one or more electrodes at or near the distal end of the lead 300. Of course, a conductor may form or connect to an electrode at the distal end or at any point between the proximal end and the distal end. The channels 312, 312' are defined by the lead body 304 or optionally formed by conduits embedded in the lead body 304. As described below, the channels 312, 312' can help direct flow of adhesive material, for example, from a reservoir to a site. Of course, a channel may function as a reservoir. The radiation conduit 316 allows for delivery of radiation from a source to a site. For example, a fiber may serve as a conduit capable of delivering ultraviolet, visible and/or infrared radiation from a source to a site. Also consider a waveguide or a conductor capable of delivering RF or microwave radiation from a source to a site. As such, an exemplary lead optionally includes a waveguide for delivery of radiation. Such a waveguide is optionally of a particular dimension (e.g., diameter, height, width, length, etc.) to facilitate efficient and/or effective deliver of radiation to a site.

Figure 4:
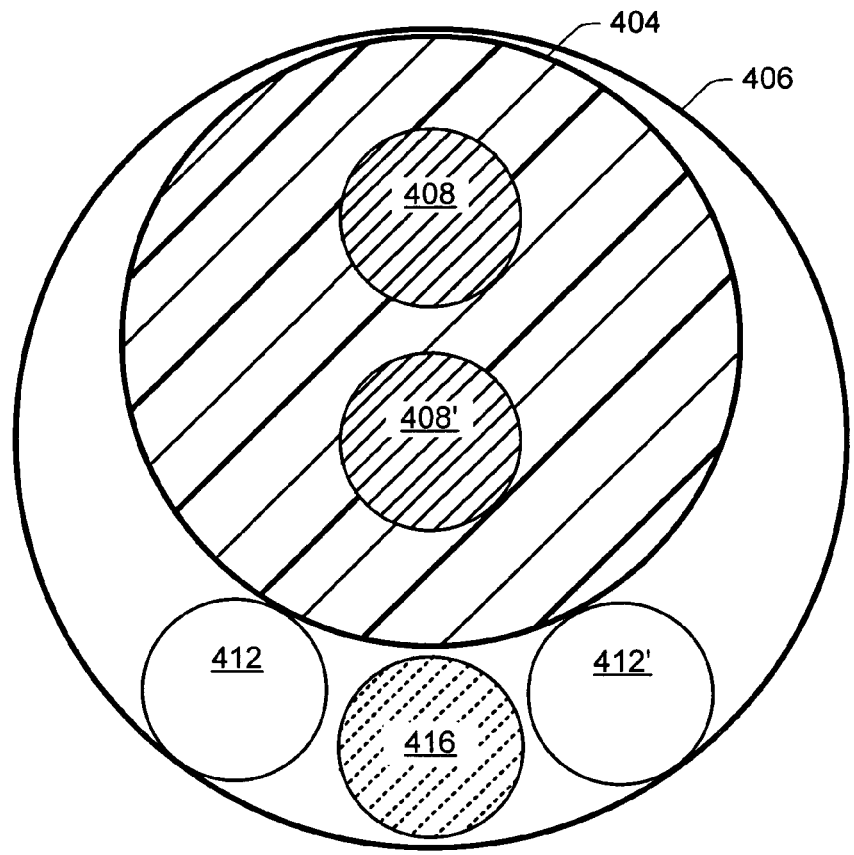
FIG. 4 is a cross-sectional view of an exemplary lead and a sheath.

FIG. 4 shows a cross-sectional view of an exemplary lead and sheath assembly 400. The lead and sheath assembly 400 has a proximal end and a distal end and, as shown in the cross-sectional view, includes one or more conductors 408, 408', one or more channels 412, 412', and optionally a radiation conduit 416. A lead body 404 houses the two conductors 408, 408' while a lead sheath 406 houses the lead body 404, the two channels 412, 412' and the radiation conduit 416. In general, a lead body and/or a sheath are constructed from flexible material that allows for navigation in a patient body or other animal body.

The conductors 408, 408' allow for connection to a stimulation device or securing device at or near the proximal end of the lead 400 and to one or more electrodes at or near the distal end of the lead 400. Of course, a conductor may form or connect to an electrode at the distal end or at any point between the proximal end and the distal end. The channels 412, 412' are formed by conduits. As described below, the channels 412, 412' can help direct flow of adhesive material, for example, from a reservoir to a site. Of course, a channel may function as a reservoir. The radiation conduit 416 allows for delivery of radiation from a source to a site. For example, a fiber may serve as a conduit capable of delivering ultraviolet, visible and/or infrared radiation from a source to a site. Also consider a waveguide or a conductor capable of delivering RF or microwave radiation from a source to a site.

The lead and sheath assembly 400 optionally allows for rotation of the lead body 404 within the sheath 406 and/or for positioning of the channels 412, 412' and/or the radiation conduit 416 within the sheath 406, for example, about the circumference of the lead body 404. Further, the assembly optionally allows for translational positioning of the sheath 406, the lead body 404, the conductors 408, 408', the channels 412, 412' and/or the radiation conduit 416 with respect to any component of the assembly 400. For example, the assembly 400 may allow for translational positioning of the lead body 404 with respect to the lead sheath 406, the channels 412, 412' and the radiation conduit 416.

Figure 5:
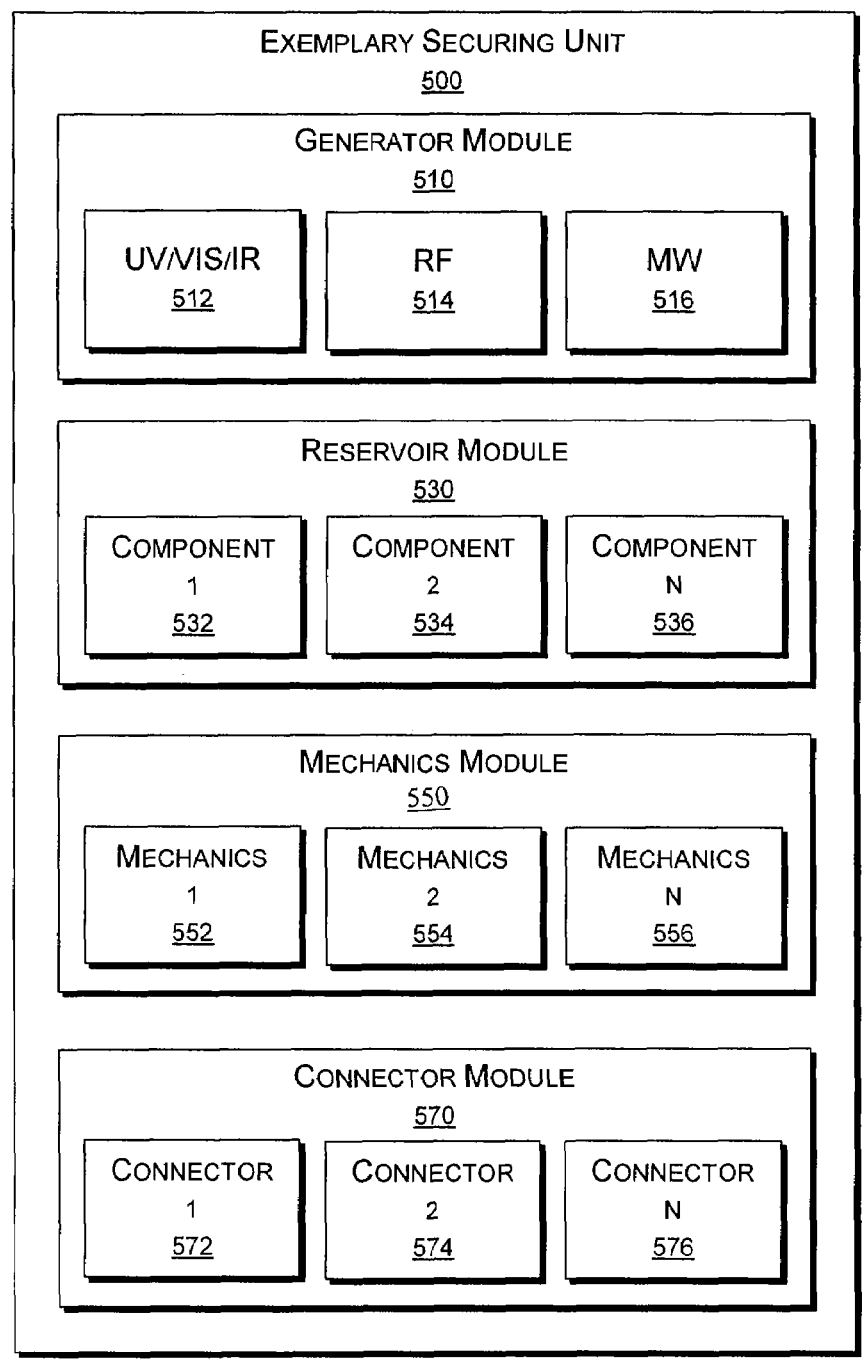
FIG. 5 is a block diagram of an exemplary securing unit.

FIG. 5 shows a securing unit 500 capable of operation with one or more exemplary leads and/or exemplary lead and sheath assemblies. The securing unit 500 includes a generator module 510, a reservoir module 530, a mechanics module 550, and a connector module 570. The generator module 510 optionally includes a ultraviolet, visible and/or infrared wavelength energy generator or generators 512, a radiofrequency wavelength energy generator 514, and/or a microwave wavelength energy generator 516. Of course, a current and/or a voltage generator, as well as other generators or sources, are also possible. For example, a battery or other power source may serve as a current or voltage generator. The reservoir module 530 includes one or more reservoirs, for example, a first component reservoir 532, a second component reservoir 534, to an nth component reservoir 536. The mechanics module 550 includes appropriate mechanics to operate one or more leads and/or lead and sheath assemblies. For example, a first mechanism 552 allows for rotation of a lead sheath about a lead body, a second mechanism 554 allows for delivering material contained in a reservoir to one or more channels of a lead, and a third mechanism allows for translation of a lead sheath with respect to a lead body. Of course, a variety of mechanisms are possible, including, but not limited to, mixing mechanisms, positioning mechanisms, tensile strength measurement mechanisms, etc.

The connector module 570 includes one or more connectors for connecting a lead, a sheath and/or other component to the securing unit 500. In general, a connector allows a component to function with respect to one or more modules of a securing unit.

Figure 6:
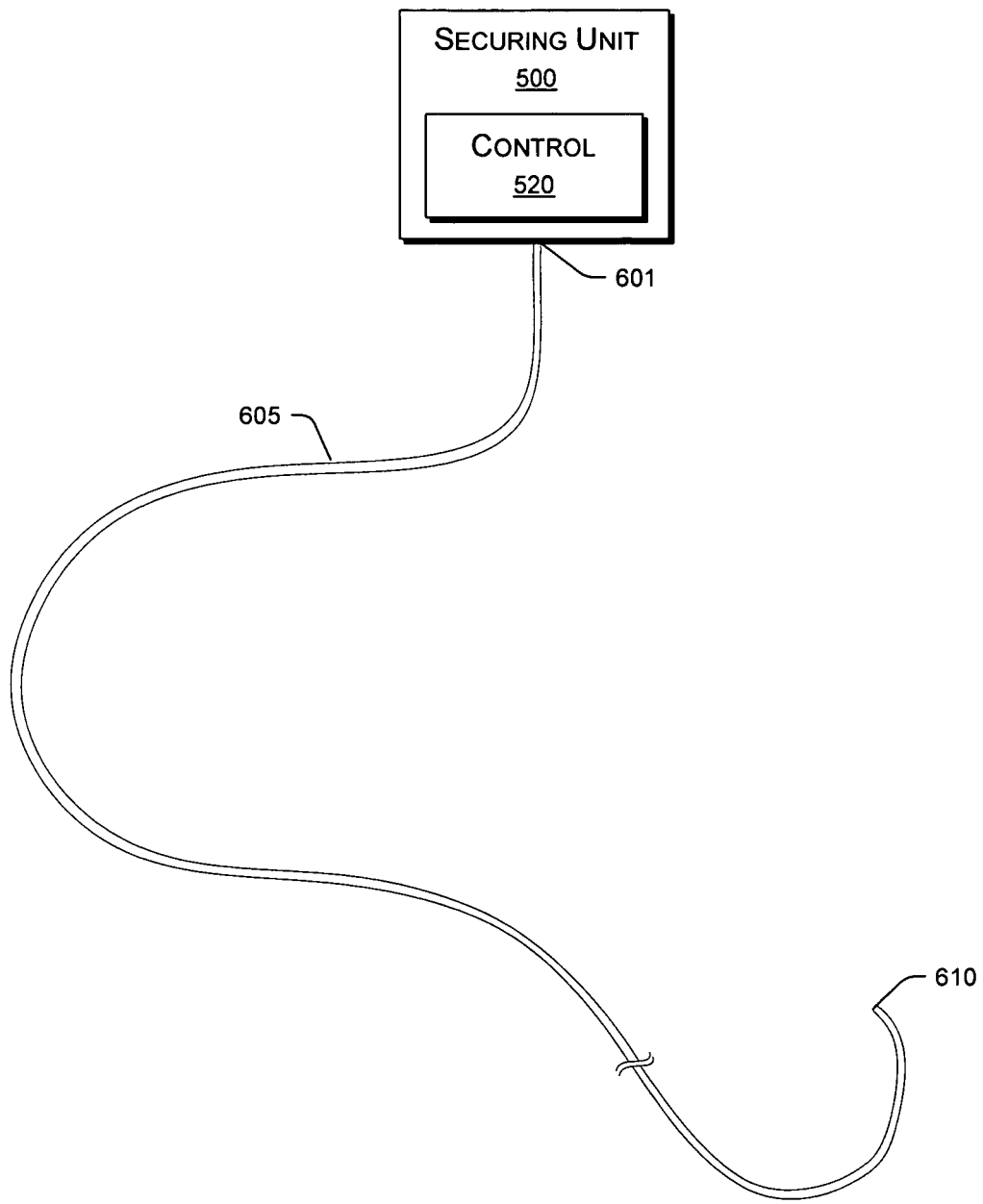
FIG. 6 is a diagram of the exemplary securing unit and an exemplary lead or an exemplary lead and a sheath.

FIG. 6 shows an exemplary system 600 that includes the exemplary securing unit 500 and an exemplary lead and/or lead and sheath assembly 605. The securing unit 500 includes a control module 520 to control various features of the securing unit 500. The lead and/or lead and sheath assembly 605 has a proximal end 601 connected to the securing unit 500 via one or more connectors and a distal end 610. The distal end 610 is positionable to a site in a patient body or animal body through use of the securing unit 500 and/or other instruments (e.g., instruments typically used in positioning a lead in a body).

Exemplary Securing Methods

Figure 7:
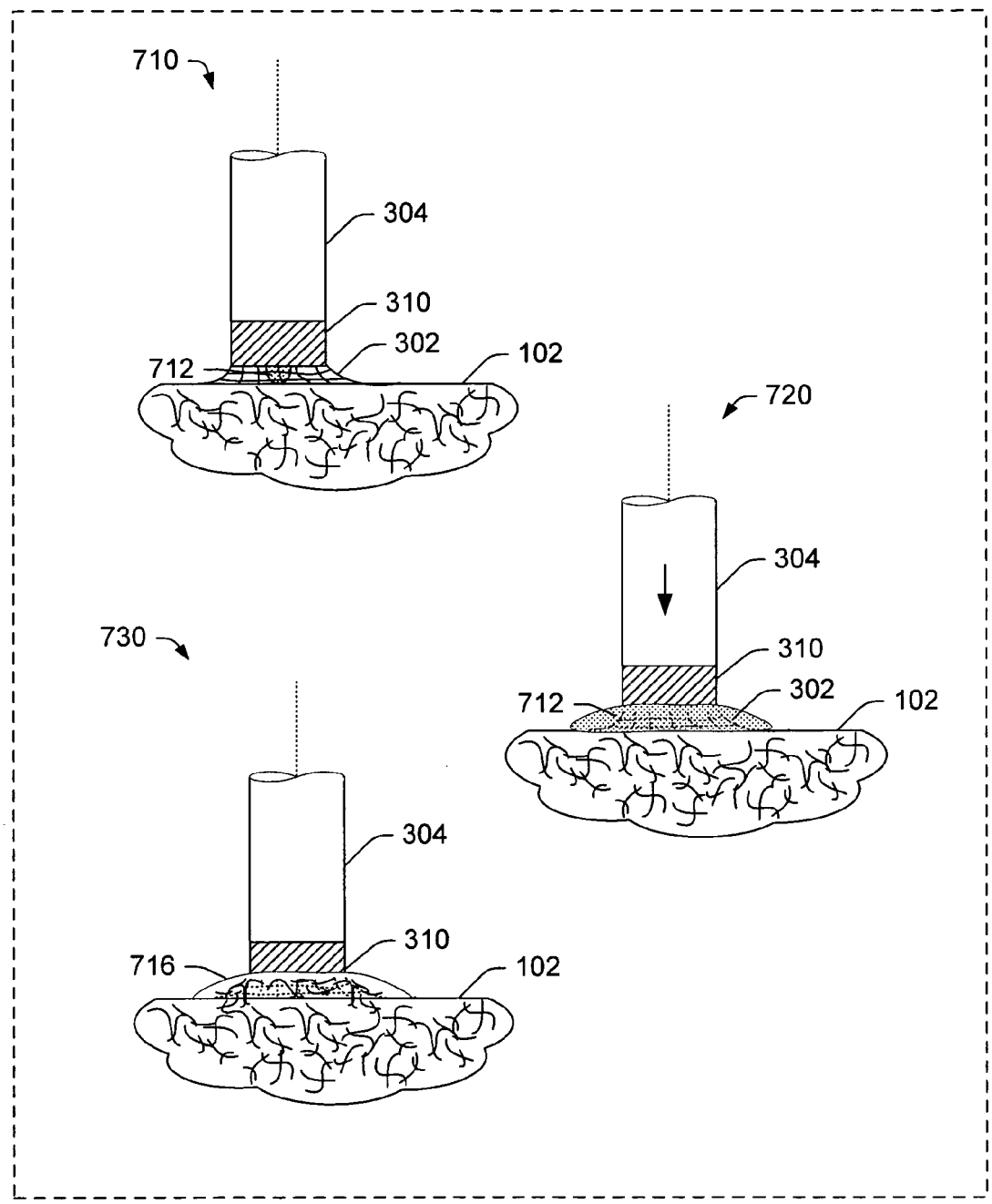
FIG. 7 illustrates an exemplary method for securing a lead to tissue using an adhesive.

FIG. 7 illustrates an exemplary method 700 for securing a distal end of a lead to a portion of tissue (e.g., nerve tissue, cardiac tissue, etc.). The exemplary lead 304 includes an electrode 310, which connects, for example, to a conductor such as one of the conductors 308, 308' shown in FIG. 3. Often, it is desirable to secure an electrode to tissue. For example, a secure electrode may help to ensure positional integrity and/or electrical contact with tissue. Of course, securing a lead at a point removed from an electrode may also help to achieve benefits. Thus, various exemplary leads and/or lead and sheath assemblies are configured to secure a lead via an electrode or via another point or points on a lead.

In this example, the electrode 310 has an associated mesh 302, which is optionally a conductive material, a biodegradable material, a radiation sensitive material, a material including an immunological agent, etc. In another example, one or more tabs or other protrusions extend from the electrode or an electrode portion wherein such protrusions optionally include an aforementioned material. Further, the mesh 302 is optionally a polymer patch style electrode or a conductive mesh electrode.

The mesh 302 is optionally composed of a material that reacts with an extruded material extruded from the lead 304, for example, the mesh may include a material that is an initiator, a reactant, accelerant, decelerant, a catalyst, etc., that causes an extruded material to polymerize or undergo another type of reaction.

Referring again to the various illustrations of FIG. 7, in an extrusion step 710, an adhesive 712 is delivered from the lead 304 to a site on the tissue 102. In the step 710, the distal end of the lead 304 and/or the mesh 302 contacts the tissue 102 or is proximate to a site on the tissue 102. After delivery of the adhesive 712, in a contact step 720, the lead is positioned to ensure contact with the tissue 102 or to ensure contact with the adhesive 712, which is in contact with the tissue 102. The contact step 720 allows the adhesive 712 to secure the lead 304 (e.g., optionally via the mesh 302) to the tissue 102 or to secure the lead 304 in a position proximate to the tissue 102. Thereafter, a tissue growth step 730 optionally follows wherein growth of tissue 716 occurs at the site where the lead 304 has been secured, which may further secure the lead 304 at the site. The mesh 302 may provide a network for tissue in-growth. Various exemplary leads include a mesh that provides a network for tissue in-growth and an additional function, such as, but not limited to, immunochemical delivery, initiation of a reaction, co-reactant of a reaction, co-conductor of an electrode, etc.

Figure 8:
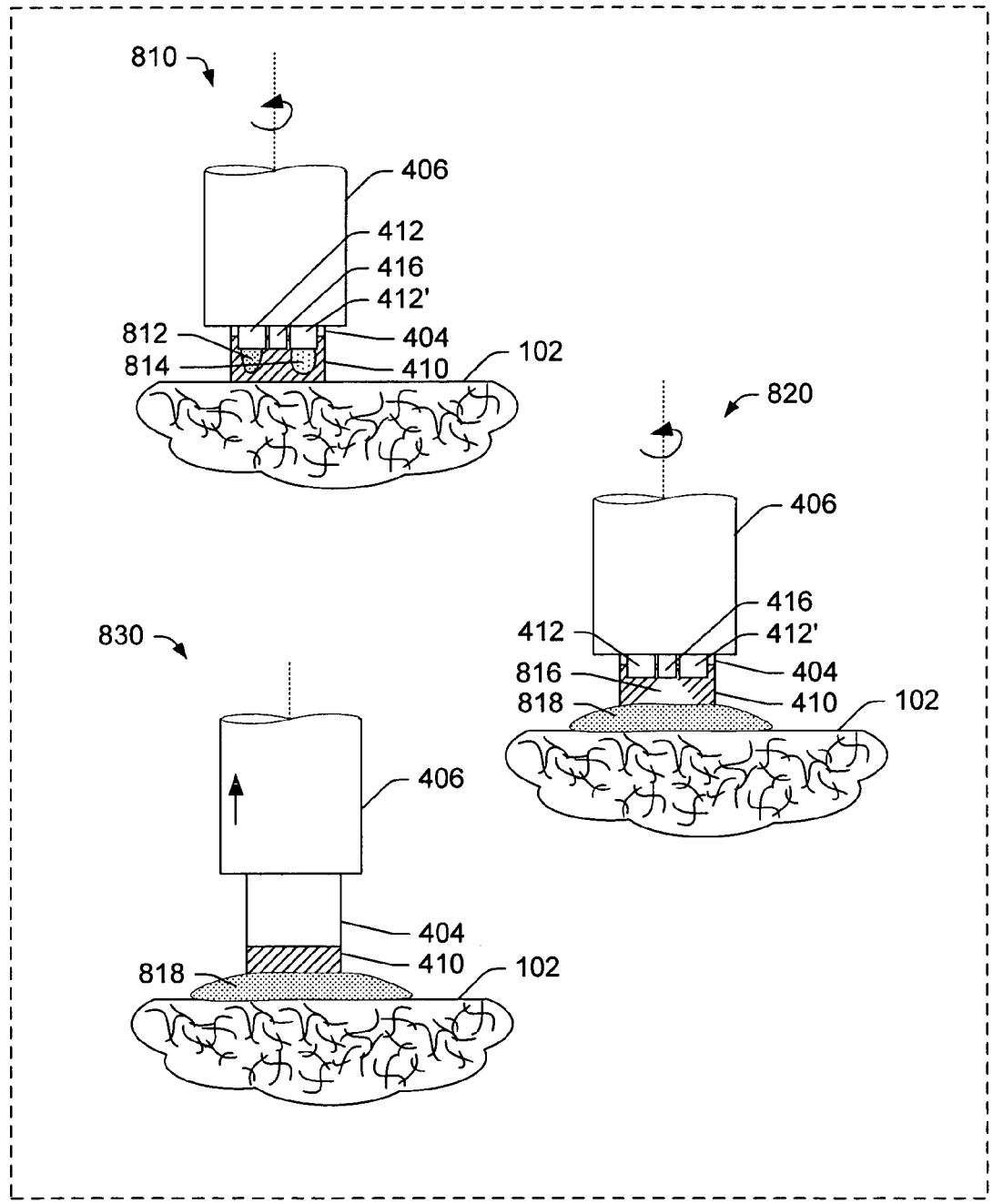
FIG. 8 illustrates an exemplary method for securing a lead to tissue using an adhesive using ultraviolet radiation to initiate, decelerate, and/or accelerate curing of an adhesive.

FIG. 8 illustrates an exemplary method 800 for securing a distal end of a lead to a portion of tissue (e.g., nerve tissue, cardiac tissue, etc.). The exemplary lead 404 includes an electrode 410, which connects, for example, to a conductor such as one of the conductors 408, 408' shown in FIG. 4. Often, it is desirable to secure an electrode to tissue. For example, a secure electrode may help to ensure positional integrity and/or electrical contact with tissue. Of course, securing a lead at a point removed from an electrode may also help to achieve benefits. Thus, various exemplary leads and/or lead and sheath assemblies are configured to secure a lead via an electrode or via another point or points on a lead.

In an extrusion step 810, a first chemical component 812 and a second chemical component 814 are delivered from a channel of a first conduit 412 and a channel of a second conduit 412', respectively, to tissue 102. During the step 810, the first conduit 412 and the second conduit 412' are optionally rotated about the lead 404 to allow for distribution of the first chemical component 812 and the second chemical component 814 in a region proximate to the lead 404. In another example, the lead 404 or a portion thereof proximate to a site rotates to facilitate distribution of a component or substance; of course, other examples are possible and may be suitably used where appropriate. Next, in a radiation delivery step 820, a radiation conduit 416 delivers radiation to the chemicals 818. During the step 820, the radiation conduit 416 is optionally rotated about the lead 404 to allow for distribution of radiation. The delivery of radiation may act to initiate, decelerate, and/or accelerate one or more chemical reactions involving the chemicals 818 and/or other chemicals of the tissue 102, the lead 404, the electrode 410. In general, such chemical reactions cure the chemicals 818 and thereby allow for formation of an adhesive bond between the lead 404 (e.g., the electrode 410) and the tissue 102. In turn, the formation of the adhesive bond secures the lead 404 to a site on the tissue. Of course, the method 800 (or various other exemplary methods) may secure a lead to a site within tissue.

A sheath removal step 830 occurs after delivery of the radiation delivery step 820. The sheath removal step 830 typically occurs once the chemicals have formed a sufficient adhesive bond. As described above, a securing unit optionally includes one or more mechanisms that allow for translation of a sheath 406 with respect to a lead body. Of course, the channel conduits 412, 412' and the radiation conduit 416 may also be translated by one or more mechanisms associated with a securing unit.

Figure 9:
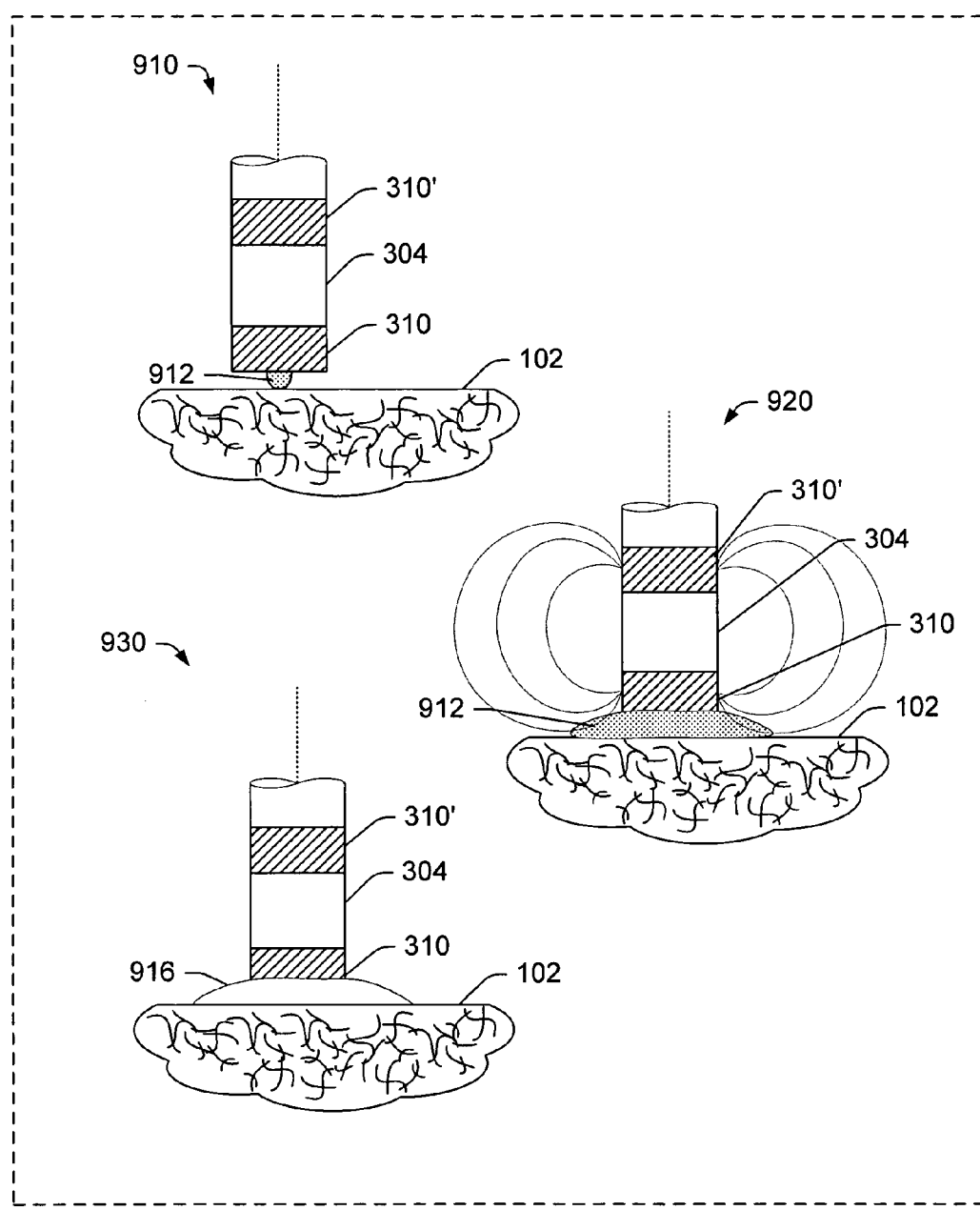
FIG. 9 illustrates an exemplary method for securing a lead to tissue using an adhesive using electromagnetic energy to initiate, decelerate, and/or accelerate curing of an adhesive.

FIG. 9 illustrates an exemplary method 900 for securing a distal end of a lead to a portion of tissue (e.g., nerve tissue, cardiac tissue, etc.). The exemplary lead 304 includes a first electrode 310 and a second electrode 310', which connect, for example, to respective conductors such as the conductors 308, 308' shown in FIG. 3. Often, it is desirable to secure an electrode to tissue. For example, a secure electrode may help to ensure positional integrity and/or electrical contact with tissue. Of course, securing a lead at a point removed from an electrode may also help to achieve benefits. Thus, various exemplary leads and/or lead and sheath assemblies are configured to secure a lead via an electrode or via another point or points on a lead.

In an extrusion step 910, a chemical component 912 is delivered from a channel of the lead 304 to tissue 102. Next, in a current or electro and/or magnetic radiation delivery step 920, the two electrodes 310, 310' form a current circuit and/or emit radiation proximate to and/or including the chemical component 912 and optionally the tissue 102. The delivery of current and/or radiation may act to initiate, decelerate, and/or accelerate one or more chemical reactions involving the chemical 912 and/or other chemicals of the tissue 102, the lead 304, the electrodes 310, 310', etc. In general, such chemical reactions cure the chemical 912 and thereby allow for formation of an adhesive bond between the lead 304 (e.g., the lead and/or one or more of the electrodes 310, 310') and the tissue 102. In turn, the formation of the adhesive bond secures the lead 304 to a site on the tissue. Of course, the method 900 (or various other exemplary methods) may secure a lead to a site within tissue. A curing step 930 allows the chemical or chemicals to cure after being subject to current and/or radiation. Tissue growth 916 optionally occurs at the site where the lead 304 is secured, which may further secure the lead 304 at the site. Tissue growth typically depends on the type of adhesive used and/or the tissue environment.

Figure 10:
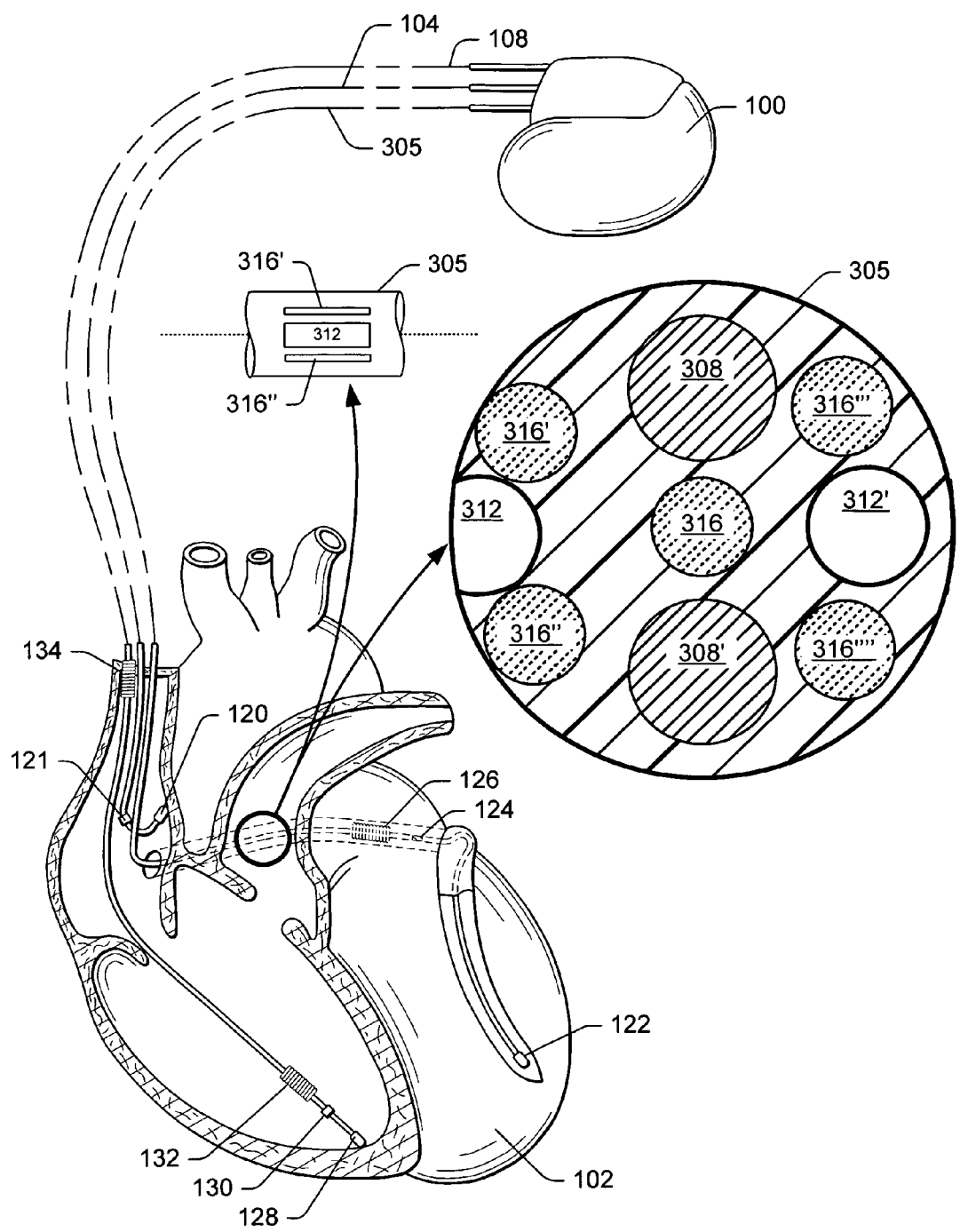
FIG. 10 is a simplified diagram illustrating an implantable stimulation device in electrical communication with at least three leads implanted into a patient's heart for delivering multi-chamber stimulation and shock therapy wherein at least one of the leads is adhered to tissue at a position between a distal end and an end in communication with the implantable device.

FIG. 10 shows an exemplary lead 305 with a lead portion adhered to tissue at a site that lies between a distal end (e.g., tip electrode 122) and an end in communication with the implantable device 100. In this example, the exemplary lead 305 includes one or more various features of other aforementioned leads. In particular, the lead 305 includes at least one channel (e.g., the channel 312, 312', etc.) capable of delivering a substance from a side of the lead 305. Such a substance is optionally an adhesive such as a polymer adhesive. Further, such a substance is optionally affected by radiation in a manner that initiates, accelerates, decelerates, etc. a chemical reaction. The exemplary lead 305 includes two radiation conduits 316, 316" substantially adjacent to the channel 312. In this manner, adhesive provided via the channel 312 may be affected by radiation provided via the radiation conduit 316 and/or the radiation conduit 316". The exemplary lead 305 also includes another channel 312' and pair of radiation conduits 316''', 316'''' that may allow for attaching the lead 305 at another point along its length.

The exemplary lead 305 may include features of the exemplary lead 304 as discussed with reference to FIG. 3. Thus, channels, conduits and/or conductors may terminate at a particular length along a lead, migrate in a radial direction or outward direction with respect to length along a lead, etc. As such, an exemplary lead may have one or more portions along a length that allow for adhering the lead or fixing the lead to tissue or even another lead (e.g., the leads 104 and/or 108) in a vessel or other location. The ability to fix a lead at one or more intermediate points between a distal and a proximate end can enhance effectiveness of the lead. Further, an exemplary lead may be fixed at a portion along the length and not at a distal end (e.g., a free floating distal end or tip). Such "side tacking" may have a particular duration to suit a particular need. Thus, various exemplary leads optionally allow for adherence to tissue at any portion of the lead whether a portion removed from an electrode, a portion between a distal end and a device end, a portion of the lead surrounding the electrode, proximate to the electrode, or at the electrode.

Exemplary Adhesives

Exemplary adhesives may be selected from a wide range of materials, including those that rely on molecular cross-linking (e.g., glues) and/or mechanical interlocking (e.g., cements). For example, adhesives optionally include collagen materials (e.g., AVITENE® adhesive, C.R. Bard, Inc., Murray Hill, N.J.; SURGICEL® adhesive, Johnson & Johnson Medical, Inc., Arlington, Tex.; GELFOAM® adhesive, Upjohn Company, Kalamazoo, Mich.) and/or other fibrin materials, which may include cryoprecipitate, thrombin, calcium, etc. Regarding fibrin materials (e.g., fibrin glues), these typically function by reproducing stages of clotting and lead to formation of a stable fibrin clot from fibrinogen. Some fibrin glues include multiple components (e.g., fibrinogen components, thrombin components, calcium components, clotting components, anti-enzymatic components, radiation active components, antibiotic components, etc.), which can be mixed together at a delivery site or shortly prior to delivery. Of course, other exemplary adhesives may also include multiple components. One exemplary fibrin-based adhesive includes a fibrinogen and thrombin component and a calcium component. Another commercially available exemplary adhesive FIBRX® adhesive (Cryolife, Inc., Kennesaw, Ga.) is a light-activated fibrin adhesive consisting of human fibrinogen and thrombin incorporating an inhibitor that retards the polymerisation of fibrinogen by thrombin to form the clot until the mixture is exposed to light. Light exposure results in evaporation of the inhibitor enabling clot formation. Yet other adhesives rely on laser assist (e.g., laser-assisted cryoprecipitate bonding, etc.).

Fibrin-based adhesives are generally compatible with the CNS and suitable for dural closure and repair of CSF leaks; thus, such adhesives are suitable for use with various exemplary devices and/or methods described herein to secure a lead to nerve tissue (e.g., CNS, autonomic (sympathetic and parasympathetic), etc.).

Yet other adhesives include gelatin-based glues (e.g., provided as or capable of forming hydrogels), such as, but not limited to, polyethylene glycol-based hydrogels (e.g., FOCALSEAL® adhesives, Focal, Inc., Lexington, Mass.), gelatin resorcinol glue (e.g., gelatin, resorcinol, formaldehyde, and optionally glutaraldhyde), which has found use in reinforcing fragile tissues of acute aortic dissections. FOCALSEAL® adhesives are provided as a liquid and polymerize to a solid gel when exposed to light. FOCALSEAL® adhesives are typically applied in stages (i) application of primer; (ii) application of sealant; and (iii) delivery of radiation, which results in polymerization in approximately 40 seconds to approximately 60 seconds, depending on conditions. FOCALSEAL® adhesives having long-term degradation (e.g., 1 year) and short-term (e.g., 6 months) degradation are commercially available. In general, the FOCALSEAL® adhesives are absorbed by the body during degradation compared to other adhesives which are not degraded or absorbed. In general, gelatin-based glues provide greater bonding strength than fibrin-based glues.

Other gelatin-hydrogel adhesives substitute formaldehyde with other cross-linking agents (e.g., carbodiimide or genipin and poly L-glutamic acid). Such adhesives optionally include catalysts, such as, water-soluble carbodiimide (WSC). WSC-catalyzed gelatin-poly L-glutamic acid adhesives have exhibited significantly higher hemostatic capability than the fibrin-based adhesives in animal experiments. Radiation activated or photochemically activated gelatin-based adhesives often include one or more photoreactive gelatin components and one or more water-soluble difunctional macromers (e.g., polyethylene glycol diacrylate, etc.). Photoreactive groups, such as, but not limited to, ultraviolet light-reactive benzophenone or visible light-reactive xanthene dyes (e.g., fluorescein sodium salt, eosin Y, rose bengal, etc.) are incorporated in gelatin and then mixed in a saline solution containing, for example, a difunctional macromer component. Where polyethylene glycol diacrylate is used as the difunctional macromer component, an adhesive hydrogel can form within approximately one minute of radiation delivery. Such an adhesive can adhere to tissues and has been used to seal effectively arteriotomies in canine abdominal or thoracic aortas.

A study by Nakayama et al., "Photocurable surgical tissue adhesive glues composed of photoreactive gelatin and poly (ethylene glycol) diacrylate", *J'Biomed Mater Res*, 48:511-21 (1999), states that such adhesive substances have "great potential application in laparoscopic surgery, as the percutaneous delivery of the glue followed by in situ photogelation will result in prompt, safe and effective haemostasis".

Exemplary adhesives may include protein engineered materials. Protein engineered polymers are typically based on DNA gene technology and may include synthetic engineered silk and elastin proteins. A strong, quick-setting, flexible, biocompatible adhesive matrix forms upon mixing such proteins with an organic crossing-linking agent. Epithelialization and healing with absorption of such an adhesive may occur at approximately one month and achieve a tissue strength equivalent to that achieved using sutures.

Cyanoacrylate adhesives include, but are not limited to, n-butyl-2-cyanoacrylate, 2-octyl cyanoacrylate, ethyl-cyanoacrylate, ethyl-2-cyanoacrylate, and isobutyl-2 cyanoacrylate.

Aforementioned exemplary adhesives are suitable for use with various exemplary devices, systems and/or methods disclosed herein and/or structural and/or functional equivalents thereof. For example, various exemplary devices, systems and/or methods include use of a cyanoacrylate and/or a fibrin glue.

CONCLUSION

Although various exemplary devices and/or methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A lead system configured for stimulating a nerve of a patient, the lead system comprising:
    a reservoir module storing a first adhesive chemical component and a second adhesive chemical component;
    a lead body having a distal end and a proximal end, the proximal end of the lead body coupled to the reservoir module;
    a conductor extending through the lead body;
    an electrode on the lead body and in electrical contact with the conductor, the electrode coupled to the nerve of the patient;
    a first adhesive channel within the lead body, the first adhesive channel directing flow of the first adhesive chemical component to tissue of the patient;
    a second adhesive channel within the lead body, the second adhesive channel directing flow of the second adhesive chemical component to the tissue of the patient;
    wherein the first chemical adhesive component and the second adhesive chemical component are delivered to the tissue at the nerve site; and
    an adhesive member adapted to fixate the lead body to tissue of the patient, the adhesive member comprising the first adhesive chemical component and the second adhesive chemical component.

2. The lead system of claim 1, wherein the adhesive channel terminates at a side opening disposed at a side of the lead body to deliver the first adhesive chemical component and the second adhesive chemical component at an intermediate region between the proximal and distal end of the lead body, and wherein the adhesive member fixates the lead at the intermediate region between the proximal and distal end of the lead body.

3. The lead system of claim 2, further comprising a radiation conduit delivering radiation to a site of the adhesive member, the radiation conduit having a side opening adjacent to the opening of the adhesive channel.

4. The lead system of claim 1, wherein the adhesive member is disposed at the nerve of the patient to establish electrical contact between the nerve and the electrode.

5. The lead system of claim system of claim 1, wherein the first adhesive chemical component and the second adhesive chemical component are liquids.

6. The lead system of claim system of claim 1, further comprising a securing unit coupled to the proximal end of the lead body, wherein the securing unit houses the reservoir module, a generator module, a mechanics module, and a connector module.

7. A lead system configured for stimulating a nerve of a patient, the lead system comprising:

a reservoir module storing an adhesive or an adhesive component;

a lead body having a proximal end and a distal end, the reservoir coupled to the proximal end of the lead body;

at least one conductor extending through the lead body;

at least one electrode on the lead body and in electrical contact with the at least one conductor;

one or more channels that allow for a flow of the adhesive or adhesive component to a nerve site to establish electrical contact between the nerve and the at least one electrode;

an adhesive member adaptive to fixate the lead body to tissue of the patient, the adhesive member comprising the adhesive or adhesive component to the nerve; wherein the one or more channels comprises a first channel and a second channel, the first channel allowing flow of a first chemical component of the adhesive or the adhesive component and the second channel allowing flow of a second chemical component of the adhesive or the adhesive component, and wherein the first chemical component and the second chemical component are delivered to the tissue at the nerve site; and a securing unit coupled to the proximal end of the lead body, wherein the securing unit houses the reservoir module, a generator module, a mechanics module, and a connector module.

8. The lead system of claim 7, further comprising a plurality of electrodes in electrical contact with the at least one conductor.

9. The lead system of claim 7, further comprising a radiation conduit capable of delivering radiation to the site.

10. The lead system of claim 9 wherein the radiation comprises a member selected from the group consisting of UV radiation, visible radiation, IR radiation, electrical radiation and/or magnetic radiation.

11. The lead system of claim 7, wherein the lead body defines the one or more channels.

12. The lead system of claim 9, wherein the lead body houses the radiation conduit.

13. The lead system of claim 7 and further comprising: a sheath surrounding the lead body.

14. The lead system of claim 13, wherein the sheath is rotatable with respect to the lead body.

15. The lead system of claim 7, wherein a distal end of the channel is adjacent to the at least one electrode, and wherein the lead body is secured to the tissue at a distal end of the lead body.

16. The lead system of claim 15, wherein the fixation member is disposed between the tissue and the at least one electrode.

17. The lead system of claim system of claim 7, wherein the adhesive or adhesive component is a liquid.

18. A lead system for securing an implantable lead in a patient, the system comprising:

a reservoir module storing an adhesive or an adhesive component;

a lead configured for stimulating a nerve of a patient, the lead comprising:

a lead body having a proximal end and a distal end;

a conductor extending through the lead body;

an electrode on the lead body and in electrical contact with the conductor, the electrode coupled to the nerve of the patient;

an adhesive channel directing flow of an adhesive or an adhesive component from the reservoir module to tissue of the patient;

wherein the adhesive channel comprises a first channel and a second channel, the first channel allowing flow of a first chemical component of the adhesive or the adhesive component and the second channel allowing flow of a second chemical component of the adhesive or the adhesive component, and wherein the first chemical component and the second chemical component are delivered to the tissue at the nerve site;

an adhesive member adapted to fixate the lead body to the tissue of the patient, the adhesive member comprising the adhesive or the adhesive component; and a securing unit coupled to the proximal end of the lead body, wherein the securing unit houses the reservoir module, a generator module, a mechanics module, and a connector module.

19. The lead system of claim 18, wherein the generator module delivers radiation to a site of the adhesive member.

20. The lead system of claim system of claim 18, wherein the adhesive or adhesive component is a liquid.

* * * * *